United States Patent [19]
Guemene et al.

[11] Patent Number: 6,114,305
[45] Date of Patent: Sep. 5, 2000

[54] UTILIZATION OF PROLACTIN FOR PREVENTING AND/OR TREATING THE EXPRESSION OF BROODING BEHAVIOR IN BIRDS

[75] Inventors: Daniel Guemene, Mettray, France; David Zadworny; Costas Karatzas, both of Quebec, Canada

[73] Assignee: Institute National de la Recherche Agronomique

[21] Appl. No.: 08/737,248

[22] PCT Filed: May 3, 1995

[86] PCT No.: PCT/FR95/00576

§ 371 Date: Apr. 28, 1997

§ 102(e) Date: Apr. 28, 1997

[87] PCT Pub. No.: WO95/30760

PCT Pub. Date: Nov. 16, 1995

[30] Foreign Application Priority Data

May 5, 1994 [FR] France .................................. 94 05550

[51] Int. Cl.[7] ...................................................... A61K 38/16
[52] U.S. Cl. ..................................... 514/12; 514/2
[58] Field of Search ............................................. 514/2, 12

[56] References Cited

U.S. PATENT DOCUMENTS 4,302,386 11/1981 Stevens .

FOREIGN PATENT DOCUMENTS

WO9 408616 4/1994 WIPO .

OTHER PUBLICATIONS

Karatzas, C. N., et al, "Production and Characterization of Recombinant Turkey Prolactin", Comp. Biochem. Physiol. vol. 106B, No. 2, pp. 273–280, 1993.

Gilbert, M. S. et al, "Expression and Partial Purification of Human Prolactin in Escherichia coli.", File Server Stn Karlsruhe, File Medline Abrégé 91216317 and Int. J. Biochem (1991) 23 (1) 107–14.

Bianchi, C. Paul, "1–Pharmacology", Chemical Abstracts, vol. 97, No. 19, Nov. 8, 1982.

March, J. B., et al, "Effect of Active Immunization Against Recombinant Derived Chicken Prolactin Fusion Protein. . . ", File Server Stn Karlsruhe File Medline Abrégé 94343333 and J. Reprod Fertil (1994 May) 101 (1) 227–33.

Schmidt et al., "Chicken Egg Antibodies for Immunohistochemical Labeling of Growth Hormone. . . ", File Server Stn Karlsruhe, File Medline Abrégé 93359719 and J. Histochem Cytochem (1993 Sep.) 41 (9) 1441–6.

Wong et al, "Cloning of a Turkey Prolactin cDNA: Expression of Prolactin mRNA throughout the Reproductive Cycle of the Domestic Turkey", Chemical Abstracts, vol. 116, No. 5, Feb. 3, 1993, Abstract No. 35348k.

Karatzas C. N., et al, "Nucleotide Sequence of Turkey Prolactin", Nucleic Acids Research. vol. 18, No. 10, p. 3071.

Daniel et al. Virology 202:540–549, 1994.

*Primary Examiner*—Elizabeth Kemmerer
*Attorney, Agent, or Firm*—Schnader Harrison Segal & Lewis LLP

[57] ABSTRACT

A pharmaceutical composition for preventing and/or treating the expression of brooding behavior in a bird is disclosed, wherein the composition is comprised of a pharmaceutically acceptable vehicle in combination with one of the following: (a) an active ingredient comprising a hybrid construct comprising a carrier group and a protein, wherein said protein comprises at least one antigenic determinant for bird prolactin; (b) a microorganism which expresses the hybrid construct at its surface, or which excretes the hybrid construct; and (c) antibodies directed against at least one bird prolactin antigen site.

5 Claims, 2 Drawing Sheets

FIG. 1b

UTILIZATION OF PROLACTIN FOR PREVENTING AND/OR TREATING THE EXPRESSION OF BROODING BEHAVIOR IN BIRDS

CROSS-REFERENCE TO OTHER APPLICATIONS

This Application was filed under 35 U.S.C. §371 corresponding to PCT Application No. PCT/FR95/0056 filed on May 3, 1995 and claims priority to French Application No. 94/05550, filed on May 5, 1994.

BACKGROUND OF THE INVENTION

1. Field of the Invention

The present invention concerns new pharmaceutical compositions intended to prevent and/or treat the expression of brooding behavior in birds, and more particularly in the turkey. The invention also relates to the procedures for the preparation of these pharmaceutical compositions.

2. Background of the Related Art

The brooding or incubation period is one of the major phases in the natural reproductive cycle of birds. However, the aptitude for brooding, far from being considered a quality of breeders, is instead an unfavorable factor, inasmuch as all of the eggs to be hatched are incubated artificially. Brooding behavior still persists among several species of domestic birds, particularly among chickens, ducks, and turkeys. This behavior leads to a notable reduction in the number of incubatable eggs and thus to a very significant loss of income for the breeders.

The observation and understanding of this behavior have made it possible to develop the first ways to combat broodiness on breeding farms.

In the turkeys on a breeding farm, the first brooders are identified after the peak of production, i.e., toward the fourth week of egg-laying. In the absence of preventive actions, their number reaches a maximum toward the eighth week [1] [2] [3]. The passage from layer to brooder status is normally associated with a cessation of laying and with regression of the reproductive apparatus (ovary and oviduct). Certain morphological changes (such as narrowing of the pelvic bones and development of incubatory plates) and behavioral changes (an increase in the amount of time spent on the nest, defense of the nest, ruffled plumage, vocalizations, reduced feeding activity) can then be observed. However, the simultaneous appearance of the entire group of these changes is unusual in the turkey. Consequently, early identification of brooders is a trickier matter in this species.

The hypothesis of humoral control of the expression of brooding was advanced as early as 1927 [4]. Because an elevation of plasma concentrations of prolactin was associated with the expression of this behavior, this hormone was designated as the causal factor [5]; but this has never been formally confirmed. Recent studies using radioimmunoassay methods have confirmed that the plasma concentrations of LH [i.e., luteinizing hormone], as well as the concentrations of the ovarian steroids estradiol and progesterone, are minimal during brooding, while the plasma level of prolactin is maximal [6].

Nevertheless, it has been possible to detect several factors that affect the expression of brooding behavior.

Genetic factors were identified after it was observed that the percentage of turkeys capable of externalizing brooding behavior in a given a population varied as a function of the strain. The expression of brooding, as a quantitative characteristic, is controlled by several genes, and its transmission simultaneously involves both sex-linked factors and autosomal factors [7] [8]. An estimate indicates that the inheritability of this characteristic in the turkey is between 0.30 and 0.40 [9].

The incidence of brooding also depends on exogenous factors associated with the environment and on endogenous factors associated with the physiological condition of the birds. The most frequently cited environmental factors are the raising method, temperature, and light. The centralized integration of these exogenous stimuli and endogenous stimuli plays a determining role in the emergence of this behavior. One or more monoamines (such as dopamine or serotonin) and hypothalamic peptides (such as TRH [thyrotropin-releasing hormone] or VIP [vasoactive intestinal polypeptide]) may also be involved in the chain of mechanisms leading to brooding [10] [11]. It has also been suggested that ovarian steroids encourage the expression of brooding by stimulating the secretion of prolactin during the passage from layer status to brooder status.

On the basis of these studies, three ways of combating brooding have been developed, i.e.:

Selection,

Physical procedures; and

Drug treatments.

The implementation of rigorous selection programs, applied in conjunction with strict raising techniques, has made it possible to reduce the percentage of turkeys that express brooding on breeding farms. However, depending on the strains, 10 to 70 percent of the turkeys in a flock still express this behavior during the reproductive cycle. As a result, bird breeders are required to implement appropriate preventive and curative measures.

The physical procedures can be implemented both preventively and curatively.

Preventively speaking, the inhibitory properties of a change in the environment with regard to the expression of brooding [13] [14] [15] [16] are known. These properties can be utilized define standard raising procedures that minimize the expression of brooding. Therefore, it is desirable not to exceed a maximum density of 2 turkeys per square meter, and to have available a sufficient number of nests (e.g., one for every 5 turkeys), which will limit the act of laying on the ground, which also encourages brooding. It is also important to provide uniform lighting in the poultry house, to control the temperature (particularly by providing well-ventilated premises), to collect the eggs often (10 to 20 times a day), to remove the turkeys from the nests during collection, and to prevent access to the nests at night. For this purpose, nests are available that are equipped with a system that automatically ejects the birds and collects the eggs, thereby reducing the breeder's workload. However, these standard procedures do not completely prevent the expression of brooding.

The curative treatments utilized by the professionals are based on modifications of the breeding environment. These modifications include the use of high-intensity lights, audible signals, and/or electrical stimuli. However, the most common modification consists of placing the brooding turkeys in a foreign environment, known as the "de-brooding cage." The group version of this cage has a lattice-work floor or a floor that is littered with sand, while the individual cages constitute the most frequently used variant of this approach. A turkey generally stays in the cage for 3 to 6 days and, in all cases, is deprived of a nest in the cage.

This type of treatment induces a reduction of prolactinemia and is therefore probably effective for preventing the expression of brooding behavior over the short term [3]. Conversely, it probably does not always have the effect hoped for by breeders, particularly among turkeys that still lay after they have been identified as brooders and therefore are subjected to the treatment. The treatment of a turkey at this particular stage will induce in her an important mobilization of the bodily reserves that subsequently cause a suspension of laying in some of these birds. Therefore, this type of treatment entails the risk of blocking the actual reproductive capabilities of the turkeys that are potentially the most productive. Therefore, the brooding turkeys must be identified with the greatest care, in order to prevent the unintentional treatment of non-brooding turkeys, particularly at the beginning of the production period.

In short, these physical treatments are not truly satisfactory, and also require the installation of special facilities, at a significant cost to the breeder.

In parallel with these physical procedures, pharmacological treatments to combat brooding have also been proposed. The drugs proposed are essentially of three types, i.e., those that have a steroidogenic effect, those that stimulate the secretion of LH, and those that inhibit the secretion of prolactin.

The first tests of pharmacological treatments, consisting of the administration of steroids or of steroid analogs, had the goal of compensating for the decrease in circulatory levels of the steroids associated with brooding. This type of treatment most often includes an interruption of brooding, but also tends to delay the return to laying, due to the negative retro-control that is exerted by the steroids on the secretion of LH. Therefore, this type of drug was not selected.

The goal of treatment with drugs that stimulate the secretion of LH is to compensate for the decrease in LH that occurs during brooding. It has been shown that clomiphene citrate (an antiestrogenic substance) is active in interrupting brooding and stimulating the return to laying [17]. However, contradictory results for the efficacy of this substance have been reported by several authors [18] [1]. In particular, it has been shown that there is a decrease in the levels of LH after treatment—a development which is incompatible with a rapid return to laying [20]. It has also been observed that LHRH [luteinizing-hormone releasing hormone] is active in stimulating the secretion of LH in brooding turkeys [21] [22] [23]. However, the repeated injection of LHRH induces a desensitization of the pituitary, and does not stimulate ovarian activity in the dwarf hen [18]. Conversely, the injection of PMSG [pregnant-mare serum gonadotropin] stimulates ovarian activity in brooding turkeys, but does not induce either the interruption of brooding or a return to laying [24].

The inhibitory or stimulatory effects of several monoamines (e.g. serotonin or dopamine) and hypothalamic peptides (TRH, VIP) on the secretion of prolactin have been demonstrated in the turkey [10] [11] [25], and the utilization of substances that interfere with the synthesis, release, and/or action mechanism of these substances in order to control brooding has been the subject of various experiments. Bromocriptine, a dopamine analog that inhibits the secretion of prolactin in mammals, encourages the expression of brooding in the turkey [17]. Conversely, pimozide, which blocks the dopaminergic receptors, is effective in interrupting brooding and stimulating the return to laying [26]. However, this result cannot be obtained unless the turkey is treated during the intermediate phase between laying and brooding, with the associated implication of early identification. It has also been observed that the secretion of prolactin is stimulated by serotonin [27] [11] and by PCPA (a serotonin-synthesis inhibitor), and eventually induces eventually the interruption of brooding [28] [29]. On the other hand, the positive results that have been reported for the restoration of ovarian activity [28] have not yet been confirmed.

It has furthermore been shown that the intracerebral administration of prolactin ovine retards the entry into production of immature turkeys, and also induces nest-making behavior in laying turkeys, with an associated decrease in plasma concentrations of prolactin [30].

The most recent approaches consist of utilizing antibodies directed against VIP. The injection of such antibodies [31] induces a decrease in the plasma concentration prolactin and the interruption of brooding, but simultaneously induces a reduction in LH levels in the dwarf hen, which reduction is prejudicial to laying.

An active anti-VIP immunization strategy has also been described in the international patent application published under No. WO 94/08616. However, the results obtained by other authors with this method have been deemed ambiguous and scarcely satisfactory (Sharp, P. J., Sterling, R. J., Talbot, R. T., and Huskinson, N. S., in *J. Reprod. Fert.,* Vol. 11 (1993), pp. 38 and 66), due to the fact that although the VIP unquestionably stimulates the secretion of prolactin, it also has an effect on the secretion of LH (a hormone that is indispensable to the proper progress of reproduction). In two recent articles (in *Biol. Reprod.,* Vol. 50 (1994), pp. 1350–1356, and in *Biol. Reprod.,* Vol. 50 (1994), pp. 1344–1349), the team led by Dr. El Halawani (the inventor in the international patent application cited above) also reported the ambiguity of the role of VIP with regard to the secretion of prolactin.

A link between the variations in prolactinemia and the expression of brooding behavior has been suggested (by Etches et al., in *Poult. Sci.,* Vol. 61, Part 7 (1982), pp. 1354–1362), but no causal relationship has been formally demonstrated. Nor has any determination been made of whether the elevation in prolactinemia is the cause or the consequence of the expression of brooding, or even the simultaneous result of another mechanism. In a recent article (Guemene, D., and Williams, J. B., in *Reprod. Nutri. & Develop.,* Vol. 34 (1994), pp. 371– 381) the present inventors also demonstrated that on the contrary, depending on the raising method employed, the turkeys that expressed brooding had lower prolactin levels. It was also shown that high plasma levels of prolactin are not necessary for resumption of the expression of brooding after an interruption due to temporary deprivation of the nest (El Halawani, Burke, and Dennisson, in *Biologie et Reproduction,* Vol. 23 (1980), pp. 118–123). Thus, the latter demonstration contradicts the hypothesis regarding the causal role of prolactin.

Thus, the experimental results of the various currently available pharmacological approaches do not support or encourage the use of these approaches on breeding farms. Consequently, the physical procedures are still the only type of treatment available to breeders.

The understanding of the hormonal mechanisms associated with the expression of brooding behavior is accompanied by fundamental studies conducted in an attempt to characterize these substances, particularly prolactin [32] [33], and to identify the corresponding genes in various species of birds. Consequently, the prolactin genes for hens [34] [35] and for turkeys [36] [37] have been identified, sequenced, and cloned.

In particular, it has been proposed that the expression vector pGEX-2T [38] be utilized to produce recombinant turkey prolactin [39].

The inventors have made use of the entire above-mentioned body of academic knowledge in order to research new methods that enable the design and manufacture of pharmaceutical compositions that are capable of preventing and/or treating effectively the expression of brooding behavior in birds, and more particularly in the turkey, without inducing either a negative effect on reproduction or the continuation or resumption of laying.

This goal is reached thanks to pharmaceutical compositions that are characterized by the fact that they include, as an active ingredient, either a hybrid substance consisting of a carrier group and a protein that includes at least one antigenic determinant for prolactin, or a microorganism that expresses at its surface or excretes the said hybrid substance, or antibodies that are directed against at least one prolactin antigen site.

SUMMARY OF THE INVENTION

The present inventors have demonstrated that the antibodies that are directed against prolactin or against a modified form or a portion thereof are capable of neutralizing the circulating prolactin and also of repressing the expression of brooding behavior of in turkeys. Therefore, the present invention proposes the utilization, as active ingredients in pharmaceutical compositions, either the antibodies that are directed against at least one prolactin antigen site, or else antigen substances that reproduce at least one immunogenic characteristic of prolactin and therefore are capable of inducing, in vivo, the production of antibodies directed against the said prolactin.

The determinants and antigen sites in accordance with the invention are the ones carried by the prolactin amino-acid sequence shown in SEQ ID No. 1 in the attached sequence list.

In the pharmaceutical compositions in accordance with the invention, the active ingredient may advantageously be associated with a pharmaceutically acceptable vehicle known to those skilled in the art.

DETAILED DESCRIPTION OF THE INVENTION

Figure 1A:
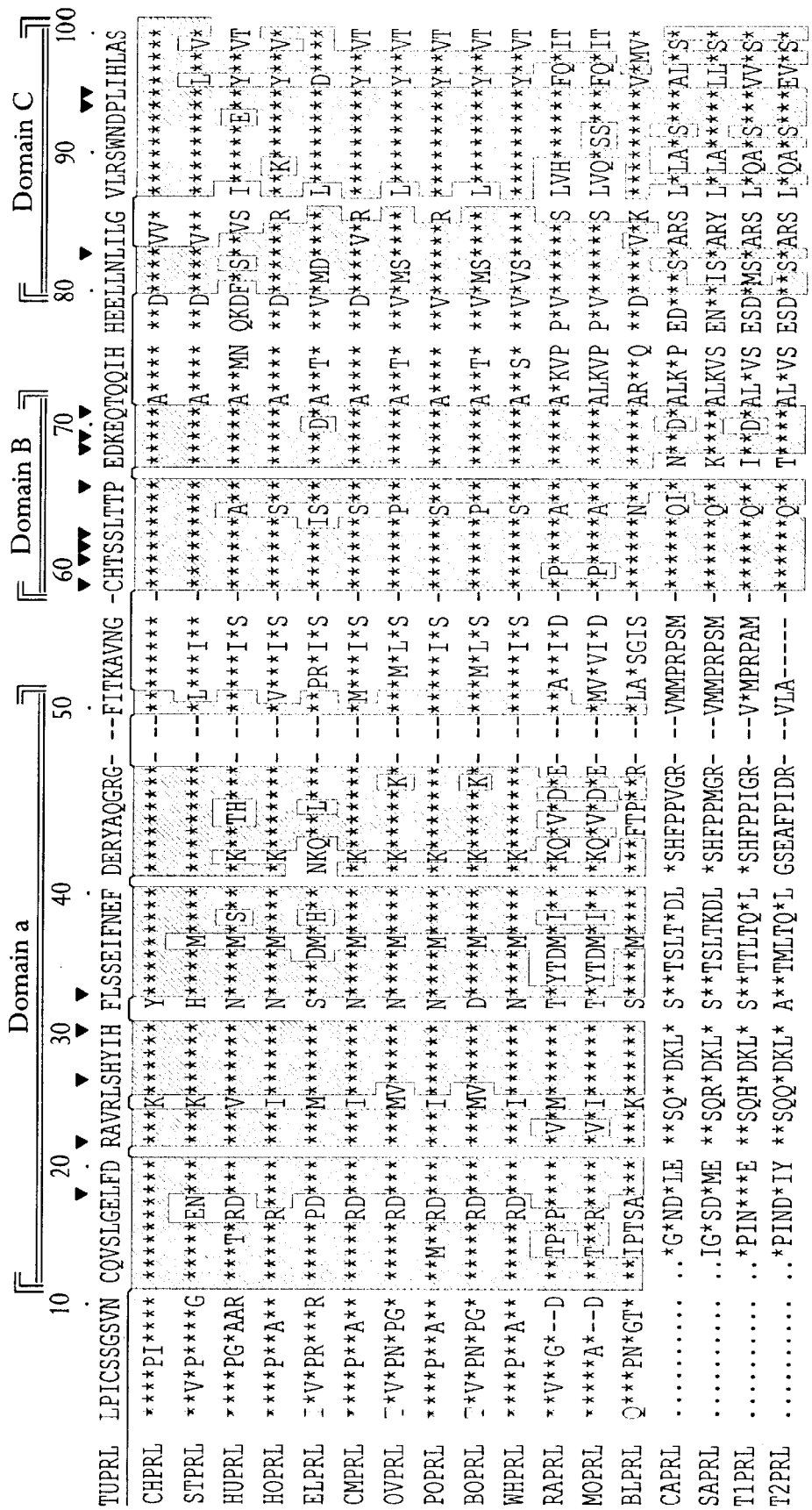
FIGS. 1a and b show a comparison of the sequence for turkey prolactin (tPRL)(SEQ ID NO:2) against the sequence for other hormones in different species, including chicken prolactin (SEQ ID NO:5); sea-turtle prolactin (SEQ ID NO:6); human prolactin (SEQ ID NO:7); horse prolactin (SEQ ID NO:8); elephant prolactin (SEQ ID NO:9); camel prolactin (SEQ ID NO:10); sheep prolactin (SEQ ID NO:11); pig prolactin (SEQ ID NO:12); cow prolactin (SEQ ID NO:13); whale-fin prolactin (SEQ ID NO:14); rat prolactin (SEQ ID NO:15); mouse prolactin (SEQ ID NO:16); frog prolactin (SEQ ID NO:17); carp prolactin (SEQ ID NO:18); salmon prolactin (SEQ ID NO:19); tilapia-1 prolactin (SEQ ID NO:20); tilapia-2 prolactin (SEQ ID NO:21); turkey growth hormone (SEQ ID NO:22); and bovine placenta lactogenic hormone (SEQ ID NO:23).

A first embodiment of a composition pharmaceutical in accordance with the invention, intended to prevent and/or treat the expression of brooding behavior in birds, consists of utilizing, as an active ingredient, a hybrid substance consisting of a protein that includes at least one antigenic determinant for prolactin and a carrier group.

Because prolactin exists in the endogenous state in birds, it was not possible to induce an immune response in these species by administering native prolactin or a portion thereof Therefore, the present inventors designed a hybrid substance that consists of the following items:

A protein that includes at least one antigenic determinant for prolactin, and

A carrier group that either does or does not exist in the endogenous state in the bird to which the pharmaceutical composition in accordance with the invention will be administered.

The association of this carrier group and of the said protein leads to a hybrid substance which does not exist in the organism of the bird, and consequently makes it possible to induce an immune response that is directed specifically against the antigenic determinant or determinants for prolactin carried by the protein associated with the carrier group.

More specifically, the present invention is supported by the techniques that have recently been implemented in molecular biology in order to produce recombinant prolactin. These techniques are based on the construction of recombinant nucleic acids that include, at a minimum, the DNA sequence that codes for prolactin, in association with a transcription promoter and/or terminator that is recognized by the enzymes of the host cell into which the said recombinant nucleic acid is introduced.

This recombinant nucleic acid is introduced into a host cell by means of vectors. The vector and the signals that control the expression of the recombinant nucleic acid are selected as a function of the eukaryotic or prokaryotic host cell in which it is placed. The vector may be a plasmid or a viral vector that is capable of infecting the host cell. The techniques that enable the cloning and expression of a recombinant nucleic acid in different host cells are known to those skilled in the art. These techniques will be illustrated in the following description of the examples, which are offered with the understanding that other vectors and host cells may be utilized.

These techniques make it possible to prepare not only a protein that is identical to the prolactin sequence, but also incomplete sequences or derivatives of the said prolactin sequence that include one or more major prolactin determinants that can be used to induce an immune response.

The present invention proposes the use of these techniques to prepare a protein that includes at least one antigenic determinant for prolactin that is fused to a carrier group following a genetic manipulation of the corresponding recombinant DNA.

The prior art includes descriptions of such manipulations whose purpose is to associate the desired protein with a carrier group (which usually consists of another protein), so as to encourage a better expression of the protein in the host cell or to cause its excretion outside the cell, or even to allow the separation and the purification of the desired protein. The hybrid substance consequently constitutes only an intermediary that is then cleaved so that the desired protein can be obtained.

This technique was implemented in order to produce recombinant prolactin by utilizing, as a carrier group, glutathione S-transferase, hereinafter referred to as "GST" [39]. In this example, the DNA that codes for turkey prolactin (tPRL), whose nucleotide sequence is shown in the attached SEQ ID No. 1, was introduced, with the aid of appropriate restriction enzymes, into the pGEX-2T plasmid [38], which carries the gene that codes for GST, under the control of a tac promoter sold commercially by the Pharmacia company. The resulting recombinant vector was utilized to transform E. coli bacteria and to cause them to express the GST-prolactin fusion protein, which was then cleaved to produce the prolactin.

The nucleic-acid sequence that codes for the GST-tPRL fusion protein and the amino-acid sequence for this protein are shown in SEQ ID No. 3 in the attached sequence list.

Those skilled in the art will be able to conceive of other vectors that are compatible with the introduction of a nucleic acid that codes for a protein which includes at least one antigenic determinant for prolactin, such as:

The pUR vector that implements the gene that codes for the lac Z protein (Ruther and Muller-Hill, in *EMBO J.*, Vol. 2 (1993), pp. 1791–1794);

The pATH vector, which implements the gene that codes for the trpE protein (Koerner et al., in *Methods in Enzymology* (1990), Genbank M32985);

The pMAL-c2 and pMAL-p2 vectors, which implement the gene that codes for the MPB protein (New England Biolabs, Lauritzen et al., *Protein Expression and Purification*, Vol. 2 (1991), pp. 372–378), and make it possible to produce a hybrid substance that is capable of inducing, in the bird, an immune response against prolactin.

Accordingly, a description has already been disclosed of the production of a hybrid substance consisting of recombinant human prolactin fused with beta-galactosidase, as has a description of the injection of this substance into rabbits in order to product antibodies directed against human prolactin (see Gilbert, M. S., et al., in *Int. J. Biochem.*, Vol. 23 (Part 1) (1991), pp. 107–114).

A variant, as used in the preparation of the hybrid substances utilized in the pharmaceutical compositions in accordance with the invention, consists of chemically coupling the carrier group with the protein that includes at least one antigenic determinant for prolactin. Kits are known to be available that can be used for this purpose, such as the kits that make it possible to couple a protein to a carrier group such as bovine serum albumin (BSA), ovalbumin, Keyhole Limpet Hemocyanine (KLH), etc.

Therefore, another goal of the invention relates to the procedures for the preparation of the pharmaceutical compositions described hereinabove.

A first procedure consists of preparing the hybrid substance that constitutes the active ingredient, through the expression of a recombinant nucleic acid that codes for a protein which includes at least one antigenic determinant for prolactin and a carrier group, and then, if desired, associating the said active ingredient with a pharmaceutically acceptable vehicle. A particular embodiment of the implementation of the foregoing procedure consists of utilizing a recombinant nucleic acid that codes for a protein which includes at least one antigenic determinant antigenic for prolactin and for GST. This procedure leads to the creation of pharmaceutical compositions that include, as an active ingredient, a fusion protein that consists of a protein which includes at least one antigenic determinant for prolactin and GST, such as GST-tPRL.

A second procedure for the preparation of the pharmaceutical composition described hereinabove consists of preparing the hybrid substance that constitutes the active ingredient through the chemical coupling of a protein which includes at least one antigenic determinant for prolactin with a carrier group, and then, if desired, associating the said active ingredient with a pharmaceutically acceptable vehicle. One particular embodiment of the implementation of the foregoing procedure consists of coupling chemically a protein which includes at least one antigenic determinant for prolactin with a carrier group that is selected from among bovine serum albumin (BSA), ovalbumin, and Keyhole Limpet Hemocyanine (KLH).

A second embodiment of a pharmaceutical composition in accordance with to invention, which is intended to prevent and/or treat the expression of brooding behavior in birds, consists of utilizing, as an active ingredient, a microorganism that is capable of expressing at its surface or of excreting a hybrid substance that consists of a carrier group and a protein which includes at least one antigenic determinant for prolactin.

This embodiment is based on the recombinant nucleic-acid technique described above. It is characterized by the implementation, as an active ingredient, of a microorganism that has been transformed by at least one recombinant nucleic acid that codes for a hybrid substance which consists of a protein that includes at least one antigenic determinant for prolactin and a heterologous carrier group. The carrier group is advantageously selected so as to allow the expression of the hybrid substance at the surface of the microorganism, or even so as to allow the secretion of the hybrid substance outside the microorganism, in order to induce an immune response against an antigenic determinant for prolactin in the bird to which the composition in accordance with the invention has been administered.

A particular embodiment of the foregoing pharmaceutical composition consists of utilizing, as an active ingredient, a bacteria or a living recombinant virus that has been transformed in the manner described hereinabove.

The bacteria and the viruses should be selected from among the ones that are known for their ability to infect birds. More specifically, from among those, bacteria and viruses should be selected that colonize the species to which the pharmaceutical composition is to be administered.

Examples include the salmonella bacteria, *E. coli*, the mycoplasms, and various viruses.

A third embodiment of a pharmaceutical composition in accordance with the invention, as intended to prevent and/or treat the expression of brooding behavior in birds, consists of utilizing, as an active ingredient, antibodies that are directed against at least one prolactin antigen site.

These antibodies may be polyclonal or monoclonal. The techniques that allow the preparation of monoclonal or polyclonal antibodies that are directed against at least one prolactin antigen site are well known to those skilled in the art (see Harlow and Lane, *Antibodies, a Laboratory Manual*, (1988) [no publisher cited], 736 pages).

The polyclonal antibodies are prepared by immunization, by injecting into an animal an appropriate quantity of prolactin (or of a modified form or a portion thereof), as prepared either by extraction and purification of a suitable biological material, or by chemical synthesis, starting with the amino-acid sequence for prolactin, or even by expression of the DNA that codes for prolactin in a host.

Accordingly, it has already been suggested that polyclonal chicken antibodies be prepared that are directed against ovine prolactin (see Schmidt, P. et al., in *J. Histochem. Cytochem.*, Vol. 41, Part 9 (1993), pp. 1441–1446).

The monoclonal antibodies may be produced by any hybridome that is prepared according to the methods for the cellular fusion of splenic cells, activated in vitro by prolactin, or a modified form or a portion thereof. Alternatively, they may be obtained from an animal that has been immunized against the said protein, and cells from a line of myelomatous cells.

The antibodies that enter into the formulation of the pharmaceutical compositions in accordance with the invention may consists of either heterologous or homologous antibodies.

The heterologous antibodies are prepared in a species other than the bird, e.g., in the rabbit, the sheep, or the horse.

The homologous antibodies are prepared in the species for which the pharmaceutical composition in accordance with the invention is intended, starting with the hybrid substance described in the first embodiment.

In addition to the active ingredient in accordance with the invention, the pharmaceutical compositions in accordance with the invention may include another active ingredient that is capable of reinforcing the immune response induced by the said first active ingredient. Examples of such supplemental active ingredients include the adjuvants that are traditionally utilized in the manufacture of vaccines.

The pharmaceutical compositions in accordance with the invention are in a form in which they can be administered, for example, by injection, in which case the pharmaceutically acceptable vehicle is an aqueous one.

The process for the administration of these pharmaceutical compositions, as well as the doses of the active ingredient, should be adapted to the type of bird to which the compositions are to be administered.

More specifically, the pharmaceutical compositions in accordance with the invention are intended to prevent and/or treat the expression of brooding behavior in the turkey. In fact, the egg-laying performance obtained in this species (i.e., approximately 110 eggs per turkey) is low compared to that of the laying strain among chicken species, specifically because of the expression of brooding behavior. However, these compositions are also useful for preventing and/or treating the expression of brooding behavior in other birds, particularly in the chicken (with egg-laying for consumption and for meat reproduction), the duck (Barbary, Peking, Mallard, etc.) the goose, and the pheasant.

Other advantages and characteristics of the invention will become clear from the following the description, which makes reference to examples of the preparation of pharmaceutical compositions intended to prevent or treat the expression of brooding behavior in the turkey, with the understanding that these examples do not constitute or impose a limitation of any kind on the purpose of the invention.

EXAMPLES

I. Production of GST-PRL

The method for producing GST-PRL was reported indirectly, as an intermediate product, in the article by KARATZAS, C. N. et al. (39: KARATZAS, C. N., GUEMENE, D., ZADWORNY, D., and KUHNLEIN, U. in *Comp. Biochem. Physiol.,* Vol. 106B (1993), pp. 273–280).

It relates to a substance that does not exist in the natural state, despite the fact that these two constituents do exist in the endogenous state in the turkey.

II. Comparison of the Sequence for Turkey Prolactin Against the Sequence for other Hormones The attached FIGS. 1*a* and *b* shows a comparison of the sequence for turkey prolactin (tPRL) against the sequence for other hormones in different species.

In this Figure:

The acids amino-acid residues that are preserved between the tPRL and the other hormones that were studied are represented by a star.

The highly homologous regions are shaded.

The five domains (a, B, C, d, and E) have been defined, starting with the residues that are always preserved.

The amino acids marked with an arrow are the ones that are preserved to a high degree in all of the proteins of vertebrates prolactin.

The helices I, II, III, and IV have been deduced from a comparison of the GH [growth hormone] of the pig and of the turkey.

The numbers correspond to the amino acids in the sequence for tPRL.

The following hormones were compared against the tPRL:

Chicken prolactin (CHPRL) (Hanke et al., 1989): 92 percent homology with turkey prolactin;

Sea-turtle prolactin (STPRL) (Yasuda et al., 1990): 84 percent homology with turkey prolactin;

Human prolactin (HUPRL) (Cooke et al., 1981): 70 percent homology with turkey prolactin;

Horse prolactin (HOPRL) (Lehrman et al., 1988): 79 percent homology with turkey prolactin;

Elephant prolactin (ELPRL) (Li et al., 1989): 67 percent homology with turkey prolactin;

Camel prolactin (CMPRL): 78 percent homology with turkey prolactin;

Sheep prolactin (OVPRL) (Adams et al., 1989): 79 percent homology with turkey prolactin;

Pig prolactin (POPRL) (Kato et al., 1990): 80 percent homology with turkey prolactin;

Cow prolactin (BOPRL) (Sasavage et al., 1982): 79 percent homology with turkey prolactin;

Whale-fin prolactin (WHPRL) (Tsubokawa et al., 1985): 83 percent homology with turkey prolactin;

Rat prolactin (RAPRL) (Cooke et al., 1980): 62 percent homology with turkey prolactin;

Mouse prolactin (MOPRL) (Harigawa et al., 1986): 56 percent homology with turkey prolactin;

Frog prolactin (BLPRL) (Takahashi et al., 1990): 71 percent homology with turkey prolactin;

Carp prolactin (CAPRL) (Yasuda et al., 1987): 34 percent homology with turkey prolactin;

Salmon prolactin (SAPRL) (Kuwana et al., 1988; Song et al., 1988): 32 percent homology with turkey prolactin;

Tilapia-1 prolactin (T1PRL) and tilapia-II prolactin (T2PRL) (Yamagushi et al., 1988): 34 and 30 percent homology with turkey prolactin, respectively;

Turkey growth hormone (TGH);

Bovine placenta lactogenic hormone (BOVPL) (Schuler and Hurley, 1987).

The above-referenced sequences are identified herein by SEQ ID NO: 5 through SEQ ID NO: 23, respectively.

This comparison of sequences made it possible to demonstrate the following points:

Six acids amino in the tPRL sequence (the serine in position 5, the glutamine in position 73, the alanine in position 142, the phenylalanine in position 147, and the acid aspartic in position 151) represent substitutions of residues that are preserved to a high degree in other vertebrates. The significance of these substitutions could not be determined, but they may be important in establishing the biological specificity of bird prolactins.

The mature tPRL contains 6 cysteines, of which two, located at the N-terminal end, have been observed in other birds, mammals, and amphibians, but not in the teleosteans or [in] hormones that are members of the CH and PL families (Nicoll et al., 1986; Kawauchi and Yasuda, 1988; Kawauchi et al, 1990; Yamakawa et al., 1990). The function of the loop between the cysteines at positions 4 and 11, in species that are superior to the fish teleosteans, is not known. It has been reported that the deletion of this disulfide loop in ovine PRL (oPRL) increases its activity in the biological quantification of fish bladder (Yamaguchi et al., 1988). This suppression has no effect on the activity of the oPRL during biological quantification of the mammary gland or of the pigeon-crop gland (Kawauchi et al., 1990).

The tPRL sequence contains three tryptophane residues, of which one, at position 91, is present in all of the prolactins, except in the mouse. Chicken and turkey prolactin contain an additional tryptophane residue in position 114, which is absent from the other vertebrate prolactins that have been characterized to date (Yamakawa et al., 1990).

The amino-acid residues consisting of cysteines at position 58, 174, 191, 199, and aspartic acid at position 178 are invariably preserved in all of the prolactins and growth hormones (see Watahiki et al, 1989a; Kawauchi and Yasuda, 1989), as well as in the PRLs like [sic] and in the placental lactogenic hormones of bovines, mouse, and rat (see Yamakawa et al., 1990). This appears to indicate that these residues are necessary in order to maintain the structural integrity of this family of genes. The specific residues of the prolactin would consequently be indispensable to the structure of this hormone and to its binding to the receptor.

This study of comparison provides indications regarding the selection of proteins which include at least one antigenic determinant for turkey prolactin and which are capable of inducing an immune response directed against the latter, during the active or passive immunization procedure described hereinabove.

III. Turkey Immunization Procedures

The treatments described hereinbelow have been of two types, i.e.:

A preventive method, referred to as "active immunization", which is implemented in the turkey before sexual maturity is reached, i.e., during the period while the birds are being raised and;

One or several methods preventive and/or curative, referred to as "passive immunization", which are implemented during the egg-laying period.

1. Active Immunization

Active immunization consisted of inducing immunization against prolactin by injecting into the turkey the hybrid GST-PRL substance produced in *E. coli* in accordance with the procedure indicated previously.

This hybrid substance then plays the role of an antigen, and causes the production of anti-PRL antibodies during the immune reaction against the GST-PRL.

a) Experimental Protocol

The experiment was carried out on turkeys raised on the ground (3 lots of 15 turkeys). The GST-PRL was administered by subcutaneous injection at multiple sites in the carina region.

The dose utilized was 100 μg per turkey and per injection, diluted in complete Freund's adjuvant (CFA) for the first injection, followed by the incomplete adjuvant (IFA) for the subsequent injections.

Four subcutaneous injections were administered at one-week intervals starting at 21 weeks of age, with intravenous follow-up injections at 28, 33, and 37 weeks of age.

The foregoing protocol preceding was experimental, and should be adapted for systematic implementation on commercial breeding farms.

In parallel, two lots of control subjects were monitored, one of which was treated according to the same protocol (i.e., with the GST alone), and the other of which received physiological serum.

b) Results

The presence of anti-prolactin antibodies in the treated turkeys was detected by means of radioimmunoassay techniques. The presence of these antibodies were not detected in any of the control turkeys.

The treated turkeys began to lay eggs after photostimulation within a period similar to the period for the control turkeys. Thus, the immunized turkeys retained their ability to lay eggs and to reproduce within the same time periods as the non-immunized turkeys.

None of the treated turkeys expressed broodiness, whereas 20 to 30 percent of the control turkeys did express broodiness.

The treated turkeys laid 4 and 5 eggs more per turkey than the control turkeys, in spite of the fact that a second follow-up vaccination was performed during the second week of laying, which was prejudicial to optimal egg-laying performance.

The presence of anti-prolactin antibodies was detected in the eggs of the treated turkeys, but did not affect the embryonic development, hatching, viability, or subsequent growth of the offspring. Because a peak in plasma levels of prolactin was associated with hatching, it was not unreasonable to expect that the presence of anti-prolactin antibodies would be prejudicial to the offspring.

Active immunization induced hyperprolactinemia starting with the first series of injections, i.e., among immature subjects (PRL>100 ng/ml instead of <10 ng/ml). Some turkeys had plasma levels of more than 1000 ng/ml. This quantification could be utilized to verify the efficacy of a production lot, or to monitor the appearance of a problem during immunization of the stock. It is also possible to verify the presence of antibodies anti-PRL in plasma by means of RIA [radioimmunoassay] tests or ELISA [enzyme-linked immunosorbent assay] methods.

2. The Passive Immunization of Turkeys

Passive immunization consisted of treating the turkeys, during the egg-laying period, with heterologous or homologous antibodies.

a) Production of Heterologous Antibodies

The heterologous antibodies were prepared in a conventional manner by injecting into a rabbit a quantity of 50 to 100 μg of purified prolactin. An intravenous follow-up was performed three weeks later, and the blood was sampled within a period of 5 to 9 days. The serum was separated for injection into the turkey.

b) Production of Homologous Antibodies

The homologous antibodies were prepared by injecting into a turkey a quantity [of] 100 μg per turkey, and by injecting purified GST-PRL. Therefore, these antibodies were identical to the ones induced during the active immunization procedure described hereinabove.

The acquisition of the antibodies can be achieved in two ways, i.e.:

Either directly, from the blood of the animal after separation of the serum; or

Starting from the yolks of eggs of turkeys that have been immunized with GST-PRL, in accordance with the procedure described hereinabove for the active immunization process.

c) Experimental Protocol

This experiment was also performed on ground-raised turkeys (2 lots of 15 turkeys), with heterologous antibodies. Rabbit serum containing anti-prolactin antibodies was administered by intramuscular injection, 3 times a week, for 4 consecutive weeks starting as of the fifth week of egg-laying, at doses of 1 ml the first week and then at doses of 0.5 ml (pure). The turkeys in the control groups received normal rabbit serum, administered in accordance with the same schedule.

d) Results

The treated turkeys did not express broodiness, whereas 45 percent of the turkeys in the group control did express broodiness.

The treated turkeys laid 8 eggs more than the turkeys in the group control.

e) Conclusions

This treatment prevented the expression of broodiness and indirectly enabled better egg-laying performances to be obtained.

It is more advantageous for the passive immunization procedure to utilize homologous antibodies, which are easier and less awkward to obtain from the eggs of turkeys that have been immunized with GST-PRL, than to start with serums from animals that have been immunized.

Therefore, the most simple method consists of incorporating, directly into the feed of the turkeys, the yolk of eggs from turkeys that have been immunized with GST-PRL.

Bibliographic References

1) NIXEY C., 1978. In: La reproduction chez la dinde. ITAVI; Paris.
2) ETCHES R. J., MCNEILLY A. S. and DUKE C. E., 1979. Poult. Scil, 58, 963–970.
3) GUEMENE D. and ETCHES R. J., 1990. Brit. Poult. Sci., 31, 847–857.
4) LIENHART R., 1927. C. R. Soc. Biol., 97, 1296–1297.
5) RIDDLE O., BATES R. W. and LAHR W. L., 1935. Am. J. Physiol., 111, 352.
6) HARVEY S. and BEDRAK E., 1984. Proc. 17th Poult. Sci. Symp., Ed. CUNNINGHAM F. J., LAKE P. E. and HEWITT T. D., Brit. Poult. Sci., 111–132.
7) MUELLER C. D. 1952. Poult. Sci., 31, 166–170.
8) SAEKI Y., 1957. Poult. Sci. 34, 378–383.
9) NESTOR K. E. 1972. Poult. Sci., 51, 86–92.
10) PROUDMAN J. A. and OPEL H., 1983. Poult. Sci. 62, 1484–1485.
11) HALL T. R., HARVEY S. and CHADWICK A., 1986. Gen. Comp. Endo., 62, 171–184.
12) EL HALAWANI M. E., SILSBY J. L. BEHNKE E. J. and FEHRER S. C. 1983. Biol Reprod., 35, 59–67.
13) BLAKELY R. M., ANDERSON R. W. and MACGREGOR H. I., 1951. Poult. Sci., 30, 907.
14) SAEKI Y. and TANABE Y., 1955. Poult. Sci., 34, 909–919.
15) NIXEY C., 1973. IVth Eur. Poult. conf., London, 87–93.
16) NESTOR K. E. BACON W. N. and RENNER P. A., 1986. Poult. Sci., 65, 1405–1409.
17) ROBINZON B., SHAFIR Z., PEREK M. and SNAPIR N., 1984. Poult. Sci., 63, 2268–2270.
18) SHARP P J., STERLIN R. C., de MILTON L., and MILLAR R. P., 1986. Brit. Poult. Sci. 27. 129–135.
19) RENNER P. A., NESTOR K. E., BACON W. N. and HAVENSTEIN G. B., 1987. Poult. Sci. 66, 558–560.
20) GUEMENE D. and ETCHES R. J., 1989a. Rep. Nat. Dev., 29, 469–476.
21) EL HALAWANI M. E., GEHRER S. C. and SILSBY J. L. 1987, Biol. Reprod., 36, 884–889.
22) GUEMENE D. and WILLIAMS J. B., 1989, J. Endocrinol., 123, 95.
23) GUEMENE D. and WILLIAMS J. B., 1992. Brit. Poult. Scil, 33, 153–163.
24) ZADWORNY D., 1985. Ph.D. Thesis, University of Guelph, 176p.
25) EL HALAWANI M. E., FEHLER S. C. and HARGIS B. M. and PORTER T., 1988. C.E.C. Crit. Rev. in Poult. Biol., 1, 284–314.
26) MILLAM J. E., BURKE W. R., EL HALAWANI M. E. and OGREN L. A., 1980. Poult. Sci. 50, 1126–1131.
27) HARGIS B. M. and BURKE W. B., 1984. Gen. Comp. Endo., 55, 12.
28) EL HALAWANI M., SILSBY J. L., BEHNKE E. J. and FEHRER S. C. 1983. Biol. Reprod., 28, 221–228.
29) GUEMENE D. and ETHCHES R. J., 1989b. Poult. Sci., 68, 1592–1594.
30) YOUNGREN O. M., EL HALAWANI M. E., SILSBY J. L. and PHILLIPS R. E., 1991. Biol. Reprod.,44, 425–491.
31) SHARP P. J., STERLING R. C., TALBOT R. T. and HUSKINSON N. S., 1989. J. Endocrinol., 122, 5–13.
32) CHENG R. W. and ETCHES R. J. 1981. J. Reprod. Fert., 62, 407–415.
33) CORCORAN D. H. and PROUDMAN J. A. 1991. Comp. Biochem. Physiol., 99 (illegible), 563–570.
34) HANKS M. C, TALBOT R. T. and SANG H. M. 1989. J. Mol. Endocr., 3, 15–21.

What is claimed is:

1. A pharmaceutical composition intended to prevent and/or treat expression of brooding behavior in a bird comprising a pharmaceutically acceptable vehicle in combination with an active ingredient comprising a hybrid construct comprising a carrier group and a protein, wherein said protein comprises at least one antigenic determinant for a bird prolactin in an amount effective to prevent and/or treat expression of brooding behavior in a bird, wherein the expression of brooding behavior is reduction or cessation of egg laying.

2. The pharmaceutical composition of claim 1 wherein said hybrid construct comprises at least one antigenic determinant of turkey prolactin.

3. The pharmaceutical composition of claim 1 wherein said active ingredient comprises the GST-tPRL fusion protein f SEQ ID NO:2 or an immunogenic determinant of the tPRL portion of said GST-tPRL fusion protein.

4. The pharmaceutical composition of claim 1 wherein said carrier group comprises glutathione-S-transferase.

5. The pharmaceutical composition of claim 4 wherein said active ingredient comprises the GST-tPRL fusion protein of SEQ ID NO:2 or an immunogenic determinant of the tPRL portion of said GST-tPRL fusion protein.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 600 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..597

(xi) SEQUENCE DESCRIPTION: SEQ ID NO:1:

| | | | | | | | | | | | | | | | | |
|---|---|---|---|---|---|---|---|---|---|---|---|---|---|---|---|---|
| TTG | CCA | ATC | TGC | TCC | AGT | GGA | TCT | GTC | AAC | TGC | CAA | GTT | TCC | CTT | GGG | 48 |
| Leu | Pro | Ile | Cys | Ser | Ser | Gly | Ser | Val | Asn | Cys | Gln | Val | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAG | CTT | TTT | GAT | CGG | GCA | GTT | AGA | CTT | TCA | CAC | TAC | ATA | CAC | TTC | CTC | 96 |
| Glu | Leu | Phe | Asp | Arg | Ala | Val | Arg | Leu | Ser | His | Tyr | Ile | His | Phe | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| TCT | TCA | GAA | ATT | TTC | AAT | GAA | TTT | GAT | GAA | CGC | TAT | GCT | CAG | GGT | CGG | 144 |
| Ser | Ser | Glu | Ile | Phe | Asn | Glu | Phe | Asp | Glu | Arg | Tyr | Ala | Gln | Gly | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| GGT | TTC | ATT | ACA | AAA | GCT | GTT | AAT | GGC | TGC | CAC | ACT | TCC | TCC | TTA | ACC | 192 |
| Gly | Phe | Ile | Thr | Lys | Ala | Val | Asn | Gly | Cys | His | Thr | Ser | Ser | Leu | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| ACT | CCT | GAA | GAT | AAG | GAG | CAA | ACT | CAG | CAG | ATT | CAT | CAC | GAA | GAG | CTA | 240 |
| Thr | Pro | Glu | Asp | Lys | Glu | Gln | Thr | Gln | Gln | Ile | His | His | Glu | Glu | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CTG | AAT | TTG | ATA | CTG | GGA | GTG | CTG | CGT | TCC | TGG | AAT | GAT | CCC | CTG | ATC | 288 |
| Leu | Asn | Leu | Ile | Leu | Gly | Val | Leu | Arg | Ser | Trp | Asn | Asp | Pro | Leu | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| CAT | CTG | GCC | TCT | GAA | GTG | CAA | AGA | ATC | AAA | GAA | GCT | CCA | GAT | ACC | ATC | 336 |
| His | Leu | Ala | Ser | Glu | Val | Gln | Arg | Ile | Lys | Glu | Ala | Pro | Asp | Thr | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| CTC | TGG | AAG | GCT | GTA | GAG | ATT | GAG | GAG | CAA | AAC | AAG | AGG | CTT | TTA | GAA | 384 |
| Leu | Trp | Lys | Ala | Val | Glu | Ile | Glu | Glu | Gln | Asn | Lys | Arg | Leu | Leu | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| GGA | ATG | GAG | AAA | ATC | GTT | GGG | CGG | ATT | CAT | TCT | GGC | GAT | GCT | GGA | AAT | 432 |
| Gly | Met | Glu | Lys | Ile | Val | Gly | Arg | Ile | His | Ser | Gly | Asp | Ala | Gly | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| GAA | GTT | TTC | TCT | CAG | TGG | GAC | GGC | CTT | CCA | TCC | CTG | CAA | CTC | GCT | GAT | 480 |
| Glu | Val | Phe | Ser | Gln | Trp | Asp | Gly | Leu | Pro | Ser | Leu | Gln | Leu | Ala | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GAG | GAC | TCC | AGA | CTC | TTT | GCT | TTT | TAC | AAC | CTG | CTG | CAT | TGC | CTC | CGC | 528 |
| Glu | Asp | Ser | Arg | Leu | Phe | Ala | Phe | Tyr | Asn | Leu | Leu | His | Cys | Leu | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| AGA | GAT | TCC | CAC | AAA | ATC | GAC | AAC | TAT | CTT | AAA | GTT | TTG | AAG | TGC | CGC | 576 |
| Arg | Asp | Ser | His | Lys | Ile | Asp | Asn | Tyr | Leu | Lys | Val | Leu | Lys | Cys | Arg | |
| | | | 180 | | | | | 185 | | | | | 190 | | | |

| | | | | | | |
|---|---|---|---|---|---|---|
| CTA | ATC | CAT | GAT | AAC | AAT | TGC TAA | 600 |
| Leu | Ile | His | Asp | Asn | Asn | Cys | |
| | | 195 | | | | | |

(2) INFORMATION FOR SEQ ID NO:2:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Leu | Pro | Ile | Cys | Ser | Ser | Gly | Ser | Val | Asn | Cys | Gln | Val | Ser | Leu | Gly |
| 1 | | | | 5 | | | | | 10 | | | | | 15 | |

| | | | | | | | | | | | | | | | |
|---|---|---|---|---|---|---|---|---|---|---|---|---|---|---|---|
| Glu | Leu | Phe | Asp | Arg | Ala | Val | Arg | Leu | Ser | His | Tyr | Ile | His | Phe | Leu |
| | | | 20 | | | | | 25 | | | | | 30 | | |

| | | | | | | | | | | | | | | | |
|---|---|---|---|---|---|---|---|---|---|---|---|---|---|---|---|
| Ser | Ser | Glu | Ile | Phe | Asn | Glu | Phe | Asp | Glu | Arg | Tyr | Ala | Gln | Gly | Arg |
| | | 35 | | | | | 40 | | | | | 45 | | | |

| | | | | | | | | | | | | | | | |
|---|---|---|---|---|---|---|---|---|---|---|---|---|---|---|---|
| Gly | Phe | Ile | Thr | Lys | Ala | Val | Asn | Gly | Cys | His | Thr | Ser | Ser | Leu | Thr |
| | 50 | | | | | 55 | | | | | 60 | | | | |

Thr Pro Glu Asp Lys Glu Gln Thr Gln Gln Ile His His Glu Glu Leu

-continued

```
                65                    70                    75                    80
            Leu Asn Leu Ile Leu Gly Val Leu Arg Ser Trp Asn Asp Pro Leu Ile
                                85                    90                    95

His Leu Ala Ser Glu Val Gln Arg Ile Lys Glu Ala Pro Asp Thr Ile
                           100                   105                   110

Leu Trp Lys Ala Val Glu Ile Glu Glu Gln Asn Lys Arg Leu Leu Glu
                           115                   120                   125

Gly Met Glu Lys Ile Val Gly Arg Ile His Ser Gly Asp Ala Gly Asn
                       130                   135                   140

Glu Val Phe Ser Gln Trp Asp Gly Leu Pro Ser Leu Gln Leu Ala Asp
            145                   150                   155                   160

Glu Asp Ser Arg Leu Phe Ala Phe Tyr Asn Leu Leu His Cys Leu Arg
                               165                   170                   175

Arg Asp Ser His Lys Ile Asp Asn Tyr Leu Lys Val Leu Lys Cys Arg
                           180                   185                   190

Leu Ile His Asp Asn Asn Cys
                       195

(2) INFORMATION FOR SEQ ID NO:3:

(i) SEQUENCE CHARACTERISTICS:
          (A) LENGTH: 1281 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..1278

(xi) SEQUENCE DESCRIPTION: SEQ ID NO:3:

ATG TCC CCT ATA CTA GGT TAT TGG AAA ATT AAG GGC CTT GTG CAA CCC         48
Met Ser Pro Ile Leu Gly Tyr Trp Lys Ile Lys Gly Leu Val Gln Pro
  1               5                  10                  15

ACT CGA CTT CTT TTG GAA TAT CTT GAA GAA AAA TAT GAA GAG CAT TTG         96
Thr Arg Leu Leu Leu Glu Tyr Leu Glu Glu Lys Tyr Glu Glu His Leu
                 20                  25                  30

TAT GAG CGC GAT GAA GGT GAT AAA TGG CGA AAC AAA AAG TTT GAA TTG        144
Tyr Glu Arg Asp Glu Gly Asp Lys Trp Arg Asn Lys Lys Phe Glu Leu
             35                  40                  45

GGT TTG GAG TTT CCC AAT CTT CCT TAT TAT ATT GAT GGT GAT GTT AAA        192
Gly Leu Glu Phe Pro Asn Leu Pro Tyr Tyr Ile Asp Gly Asp Val Lys
         50                  55                  60

TTA ACA CAG TCT ATG GCC ATC ATA CGT TAT ATA GCT GAC AAG CAC AAC        240
Leu Thr Gln Ser Met Ala Ile Ile Arg Tyr Ile Ala Asp Lys His Asn
 65                  70                  75                  80

ATG TTG GGT GGT TGT CCA AAA GAG CGT GCA GAG ATT TCA ATG CTT GAA        288
Met Leu Gly Gly Cys Pro Lys Glu Arg Ala Glu Ile Ser Met Leu Glu
                     85                  90                  95

GGA GCG GTT TTG GAT ATT AGA TAC GGT GTT TCG AGA ATT GCA TAT AGT        336
Gly Ala Val Leu Asp Ile Arg Tyr Gly Val Ser Arg Ile Ala Tyr Ser
                100                 105                 110

AAA GAC TTT GAA ACT CTC AAA GTT GAT TTT CTT AGC AAG CTA CCT GAA        384
Lys Asp Phe Glu Thr Leu Lys Val Asp Phe Leu Ser Lys Leu Pro Glu
            115                 120                 125

ATG CTG AAA ATG TTC GAA GAT CGT TTA TGT CAT AAA ACA TAT TTA AAT        432
Met Leu Lys Met Phe Glu Asp Arg Leu Cys His Lys Thr Tyr Leu Asn
        130                 135                 140
```

```
GGT GAT CAT GTA ACC CAT CCT GAC TTC ATG TTG TAT GAC GCT CTT GAT      480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA      528
Val Val Leu Tyr Met Asp Pro Met Cys Leu Asp Ala Phe Pro Lys Leu
            165                 170                 175

GTT TGT TTT AAA AAA CGT ATT GAA GCT ATC CCA CAA ATT GAT AAG TAC      576
Val Cys Phe Lys Lys Arg Ile Glu Ala Ile Pro Gln Ile Asp Lys Tyr
        180                 185                 190

TTG AAA TCC AGC AAG TAT ATA GCA TGG CCT TTG CAG GGC TGG CAA GCC      624
Leu Lys Ser Ser Lys Tyr Ile Ala Trp Pro Leu Gln Gly Trp Gln Ala
                195                 200                 205

ACG TTT GGT GGT GGC GAC CAT CCT CCA AAA TCG GAT CTG GTT CCG CGT      672
Thr Phe Gly Gly Gly Asp His Pro Pro Lys Ser Asp Leu Val Pro Arg
            210                 215                 220

GGA TCC TCC TTG CCA ATC TGC TCC AGT GGA TCT GTC AAC TGC CAA GTT      720
Gly Ser Ser Leu Pro Ile Cys Ser Ser Gly Ser Val Asn Cys Gln Val
225                 230                 235                 240

TCC CTT GGG GAG CTT TTT GAT CGG GCA GTT AGA CTT TCA CAC TAC ATA      768
Ser Leu Gly Glu Leu Phe Asp Arg Ala Val Arg Leu Ser His Tyr Ile
            245                 250                 255

CAC TTC CTC TCT TCA GAA ATT TTC AAT GAA TTT GAT GAA CGC TAT GCT      816
His Phe Leu Ser Ser Glu Ile Phe Asn Glu Phe Asp Glu Arg Tyr Ala
        260                 265                 270

CAG GGT CGG GGT TTC ATT ACA AAA GCT GTT AAT GGC TGC CAC ACT TCC      864
Gln Gly Arg Gly Phe Ile Thr Lys Ala Val Asn Gly Cys His Thr Ser
            275                 280                 285

TCC TTA ACC ACT CCT GAA GAT AAG GAG CAA ACT CAG CAG ATT CAT CAC      912
Ser Leu Thr Thr Pro Glu Asp Lys Glu Gln Thr Gln Gln Ile His His
        290                 295                 300

GAA GAG CTA CTG AAT TTG ATA CTG GGA GTG CTG CGT TCC TGG AAT GAT      960
Glu Glu Leu Leu Asn Leu Ile Leu Gly Val Leu Arg Ser Trp Asn Asp
305                 310                 315                 320

CCC CTG ATC CAT CTG GCC TCT GAA GTG CAA AGA ATC AAA GAA GCT CCA     1008
Pro Leu Ile His Leu Ala Ser Glu Val Gln Arg Ile Lys Glu Ala Pro
            325                 330                 335

GAT ACC ATC CTC TGG AAG GCT GTA GAG ATT GAG GAG CAA AAC AAG AGG     1056
Asp Thr Ile Leu Trp Lys Ala Val Glu Ile Glu Glu Gln Asn Lys Arg
        340                 345                 350

CTT TTA GAA GGA ATG GAG AAA ATC GTT GGG CGG ATT CAT TCT GGC GAT     1104
Leu Leu Glu Gly Met Glu Lys Ile Val Gly Arg Ile His Ser Gly Asp
            355                 360                 365

GCT GGA AAT GAA GTT TTC TCT CAG TGG GAC GGC TTA CCA TCC CTG CAA     1152
Ala Gly Asn Glu Val Phe Ser Gln Trp Asp Gly Leu Pro Ser Leu Gln
        370                 375                 380

CTC GCT GAT GAG GAC TCC AGA CTC TTT GCT TTT TAC AAC CTG CTG CAT     1200
Leu Ala Asp Glu Asp Ser Arg Leu Phe Ala Phe Tyr Asn Leu Leu His
385                 390                 395                 400

TGC CTC CGC AGA GAT TCC CAC AAA ATC GAC AAC TAT CTT AAA GTT TTG     1248
Cys Leu Arg Arg Asp Ser His Lys Ile Asp Asn Tyr Leu Lys Val Leu
            405                 410                 415

AAG TGC CGC CTA ATC CAT GAT AAC AAT TGC TAA                         1281
Lys Cys Arg Leu Ile His Asp Asn Asn Cys
                420                 425

(2) INFORMATION FOR SEQ ID NO:4:

(i) SEQUENCE CHARACTERISTICS:
        (A) LENGTH: 426 amino acids
        (B) TYPE: amino acid
        (D) TOPOLOGY: linear
```

(ii) MOLECULE TYPE: protein (xi) SEQUENCE DESCRIPTION: SEQ ID NO:4:

| Met | Ser | Pro | Ile | Leu | Gly | Tyr | Trp | Lys | Ile | Lys | Gly | Leu | Val | Gln | Pro |
|---|---|---|---|---|---|---|---|---|---|---|---|---|---|---|---|
| 1 | | | | 5 | | | | | 10 | | | | | 15 | |

| Thr | Arg | Leu | Leu | Leu | Glu | Tyr | Leu | Glu | Glu | Lys | Tyr | Glu | Glu | His | Leu |
|---|---|---|---|---|---|---|---|---|---|---|---|---|---|---|---|
| | | | | 20 | | | | | 25 | | | | | 30 | |

| Tyr | Glu | Arg | Asp | Glu | Gly | Asp | Lys | Trp | Arg | Asn | Lys | Lys | Phe | Glu | Leu |
|---|---|---|---|---|---|---|---|---|---|---|---|---|---|---|---|
| | | 35 | | | | | 40 | | | | | 45 | | | |

| Gly | Leu | Glu | Phe | Pro | Asn | Leu | Pro | Tyr | Tyr | Ile | Asp | Gly | Asp | Val | Lys |
|---|---|---|---|---|---|---|---|---|---|---|---|---|---|---|---|
| | 50 | | | | | 55 | | | | | 60 | | | | |

| Leu | Thr | Gln | Ser | Met | Ala | Ile | Ile | Arg | Tyr | Ile | Ala | Asp | Lys | His | Asn |
|---|---|---|---|---|---|---|---|---|---|---|---|---|---|---|---|
| 65 | | | | | 70 | | | | | 75 | | | | | 80 |

| Met | Leu | Gly | Gly | Cys | Pro | Lys | Glu | Arg | Ala | Glu | Ile | Ser | Met | Leu | Glu |
|---|---|---|---|---|---|---|---|---|---|---|---|---|---|---|---|
| | | | | 85 | | | | | 90 | | | | | 95 | |

| Gly | Ala | Val | Leu | Asp | Ile | Arg | Tyr | Gly | Val | Ser | Arg | Ile | Ala | Tyr | Ser |
|---|---|---|---|---|---|---|---|---|---|---|---|---|---|---|---|
| | | | 100 | | | | | 105 | | | | | 110 | | |

| Lys | Asp | Phe | Glu | Thr | Leu | Lys | Val | Asp | Phe | Leu | Ser | Lys | Leu | Pro | Glu |
|---|---|---|---|---|---|---|---|---|---|---|---|---|---|---|---|
| | | 115 | | | | | 120 | | | | | 125 | | | |

| Met | Leu | Lys | Met | Phe | Glu | Asp | Arg | Leu | Cys | His | Lys | Thr | Tyr | Leu | Asn |
|---|---|---|---|---|---|---|---|---|---|---|---|---|---|---|---|
| | 130 | | | | | 135 | | | | | 140 | | | | |

| Gly | Asp | His | Val | Thr | His | Pro | Asp | Phe | Met | Leu | Tyr | Asp | Ala | Leu | Asp |
|---|---|---|---|---|---|---|---|---|---|---|---|---|---|---|---|
| 145 | | | | | 150 | | | | | 155 | | | | | 160 |

| Val | Val | Leu | Tyr | Met | Asp | Pro | Met | Cys | Leu | Asp | Ala | Phe | Pro | Lys | Leu |
|---|---|---|---|---|---|---|---|---|---|---|---|---|---|---|---|
| | | | | 165 | | | | | 170 | | | | | 175 | |

| Val | Cys | Phe | Lys | Lys | Arg | Ile | Glu | Ala | Ile | Pro | Gln | Ile | Asp | Lys | Tyr |
|---|---|---|---|---|---|---|---|---|---|---|---|---|---|---|---|
| | | | 180 | | | | | 185 | | | | | 190 | | |

| Leu | Lys | Ser | Ser | Lys | Tyr | Ile | Ala | Trp | Pro | Leu | Gln | Gly | Trp | Gln | Ala |
|---|---|---|---|---|---|---|---|---|---|---|---|---|---|---|---|
| | | 195 | | | | | 200 | | | | | 205 | | | |

| Thr | Phe | Gly | Gly | Gly | Asp | His | Pro | Pro | Lys | Ser | Asp | Leu | Val | Pro | Arg |
|---|---|---|---|---|---|---|---|---|---|---|---|---|---|---|---|
| | 210 | | | | | 215 | | | | | 220 | | | | |

| Gly | Ser | Ser | Leu | Pro | Ile | Cys | Ser | Ser | Gly | Ser | Val | Asn | Cys | Gln | Val |
|---|---|---|---|---|---|---|---|---|---|---|---|---|---|---|---|
| 225 | | | | | 230 | | | | | 235 | | | | | 240 |

| Ser | Leu | Gly | Glu | Leu | Phe | Asp | Arg | Ala | Val | Arg | Leu | Ser | His | Tyr | Ile |
|---|---|---|---|---|---|---|---|---|---|---|---|---|---|---|---|
| | | | | 245 | | | | | 250 | | | | | 255 | |

| His | Phe | Leu | Ser | Ser | Glu | Ile | Phe | Asn | Glu | Phe | Asp | Glu | Arg | Tyr | Ala |
|---|---|---|---|---|---|---|---|---|---|---|---|---|---|---|---|
| | | | 260 | | | | | 265 | | | | | 270 | | |

| Gln | Gly | Arg | Gly | Phe | Ile | Thr | Lys | Ala | Val | Asn | Gly | Cys | His | Thr | Ser |
|---|---|---|---|---|---|---|---|---|---|---|---|---|---|---|---|
| | | 275 | | | | | 280 | | | | | 285 | | | |

| Ser | Leu | Thr | Thr | Pro | Glu | Asp | Lys | Glu | Gln | Thr | Gln | Gln | Ile | His | His |
|---|---|---|---|---|---|---|---|---|---|---|---|---|---|---|---|
| | 290 | | | | | 295 | | | | | 300 | | | | |

| Glu | Glu | Leu | Leu | Asn | Leu | Ile | Leu | Gly | Val | Leu | Arg | Ser | Trp | Asn | Asp |
|---|---|---|---|---|---|---|---|---|---|---|---|---|---|---|---|
| 305 | | | | | 310 | | | | | 315 | | | | | 320 |

| Pro | Leu | Ile | His | Leu | Ala | Ser | Glu | Val | Gln | Arg | Ile | Lys | Glu | Ala | Pro |
|---|---|---|---|---|---|---|---|---|---|---|---|---|---|---|---|
| | | | | 325 | | | | | 330 | | | | | 335 | |

| Asp | Thr | Ile | Leu | Trp | Lys | Ala | Val | Glu | Ile | Glu | Gln | Asn | Lys | Arg |
|---|---|---|---|---|---|---|---|---|---|---|---|---|---|---|
| | | | 340 | | | | | 345 | | | | | 350 | |

| Leu | Leu | Glu | Gly | Met | Glu | Lys | Ile | Val | Gly | Arg | Ile | His | Ser | Gly | Asp |
|---|---|---|---|---|---|---|---|---|---|---|---|---|---|---|---|
| | | 355 | | | | | 360 | | | | | 365 | | | |

| Ala | Gly | Asn | Glu | Val | Phe | Ser | Gln | Trp | Asp | Gly | Leu | Pro | Ser | Leu | Gln |
|---|---|---|---|---|---|---|---|---|---|---|---|---|---|---|---|
| | 370 | | | | | 375 | | | | | 380 | | | | |

| Leu | Ala | Asp | Glu | Asp | Ser | Arg | Leu | Phe | Ala | Phe | Tyr | Asn | Leu | Leu | His |
|---|---|---|---|---|---|---|---|---|---|---|---|---|---|---|---|
| 385 | | | | | 390 | | | | | 395 | | | | | 400 |

```
Cys Leu Arg Arg Asp Ser His Lys Ile Asp Asn Tyr Leu Lys Val Leu
                405                 410                 415

Lys Cys Arg Leu Ile His Asp Asn Asn Cys
        420                 425

(2) INFORMATION FOR SEQ ID NO:5:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Leu Pro Ile Cys Pro Ile Gly Ser Val Asn Cys Gln Val Ser Leu Gly
1               5                   10                  15

Glu Leu Phe Asp Arg Ala Val Lys Leu Ser His Tyr Ile His Tyr Leu
            20                  25                  30

Ser Ser Glu Ile Phe Asn Glu Phe Asp Glu Arg Tyr Ala Gln Gly Arg
        35                  40                  45

Gly Phe Ile Thr Lys Ala Val Asn Gly Cys His Thr Ser Ser Leu Thr
    50                  55                  60

Thr Pro Glu Asp Lys Glu Gln Ala Gln Gln Ile His His Glu Asp Leu
65                  70                  75                  80

Leu Asn Leu Val Val Gly Val Leu Arg Ser Trp Asn Asp Pro Leu Ile
                85                  90                  95

His Leu Ala Ser Glu Val Gln Arg Ile Lys Glu Ala Pro Asp Thr Ile
            100                 105                 110

Leu Trp Lys Ala Val Glu Ile Glu Gln Asn Lys Arg Leu Leu Glu
        115                 120                 125

Gly Met Glu Lys Ile Val Gly Arg Val His Ser Gly His Ala Gly Asn
130                 135                 140

Glu Ile Tyr Ser His Ser Asp Gly Leu Pro Ser Leu Gln Leu Ala Asp
145                 150                 155                 160

Glu Asp Ser Arg Leu Phe Ala Phe Tyr Asn Leu Leu His Cys His Arg
            165                 170                 175

Arg Asp Ser His Lys Ile Asp Asn Tyr Leu Lys Val Leu Lys Cys Arg
            180                 185                 190

Leu Ile His Asp Ser Asn Cys
        195

(2) INFORMATION FOR SEQ ID NO:6:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Leu Pro Val Cys Pro Ser Gly Ser Val Gly Cys Gln Val Ser Leu Glu
1               5                   10                  15

Asn Leu Phe Asp Arg Ala Val Lys Leu Ser His Tyr Ile His His Leu
            20                  25                  30

Ser Ser Glu Met Phe Asn Glu Phe Asp Glu Arg Tyr Ala Gln Gly Arg
```

```
                35                  40                  45
Gly Phe Leu Thr Lys Ala Ile Asn Gly Cys His Thr Ser Ser Leu Thr
        50                  55                  60
Thr Pro Glu Asp Lys Glu Gln Ala Gln Gln Ile His His Glu Asp Leu
65                  70                  75                  80
Leu Asn Leu Val Leu Gly Val Leu Arg Ser Trp Asn Asp Pro Leu Leu
                85                  90                  95
His Leu Val Ser Glu Val Gln Ser Ile Lys Glu Ala Pro Asp Thr Ile
            100                 105                 110
Leu Lys Ala Val Glu Ile Glu Glu Gln Asp Lys Arg Leu Leu Glu Gly
            115                 120                 125
Met Glu Lys Ile Val Gly Gln Val His Pro Gly Glu Ile Glu Asn Glu
            130                 135                 140
Leu Tyr Ser Pro Trp Ser Gly Leu Glu Ser Leu Gln Gln Val Asp Glu
145                 150                 155                 160
Asp Ser Arg Leu Phe Ala Phe Tyr Asn Leu Leu His Cys Leu Arg Arg
                165                 170                 175
Asp Ser His Lys Ile Asp Asn Tyr Leu Lys Leu Lys Cys Arg Leu
            180                 185                 190
Ile His Asp Asn Asn Cys
            195

(2) INFORMATION FOR SEQ ID NO:7:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Leu Pro Ile Cys Pro Gly Gly Ala Ala Arg Cys Gln Val Thr Leu Arg
1               5                   10                  15
Asp Leu Phe Asp Arg Ala Val Val Leu Ser His Tyr Ile His Asn Leu
                20                  25                  30
Ser Ser Glu Met Phe Ser Glu Phe Asp Lys Arg Tyr Thr His Gly Arg
            35                  40                  45
Gly Phe Ile Thr Lys Ala Ile Asn Ser Cys His Thr Ser Ser Leu Ala
        50                  55                  60
Thr Pro Glu Asp Lys Glu Gln Ala Gln Met Asn Gln Lys Asp Phe
65                  70                  75                  80
Leu Ser Leu Ile Val Ser Ile Leu Arg Ser Trp Asn Glu Pro Leu Tyr
                85                  90                  95
His Leu Val Thr Glu Val Arg Gly Met Gln Glu Ala Pro Glu Ala Ile
            100                 105                 110
Leu Ser Lys Ala Val Glu Ile Glu Glu Gln Thr Lys Arg Leu Leu Glu
            115                 120                 125
Gly Met Glu Leu Ile Val Ser Gln Val His Pro Glu Thr Lys Glu Asn
            130                 135                 140
Glu Ile Tyr Pro Val Trp Ser Gly Leu Pro Ser Leu Gln Met Ala Asp
145                 150                 155                 160
Glu Glu Ser Arg Leu Ser Ala Tyr Tyr Asn Leu Leu His Cys Leu Arg
                165                 170                 175
Arg Asp Ser His Lys Ile Asp Asn Tyr Leu Lys Leu Leu Lys Cys Arg
```

```
            180                 185                 190
Ile Ile His Asn Asn Cys
        195

(2) INFORMATION FOR SEQ ID NO:8:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Leu Pro Ile Cys Pro Ser Gly Ala Val Asn Cys Gln Val Ser Leu Arg
1               5                  10                  15

Glu Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Val Thr Lys Ala Ile Asn Ser Cys His Thr Ser Ser Leu Ser
    50                  55                  60

Thr Pro Glu Asp Lys Glu Gln Ala Gln Gln Ile His His Glu Asp Leu
65                  70                  75                  80

Leu Asn Leu Ile Leu Arg Val Leu Lys Ser Trp Asn Asp Pro Leu Tyr
                85                  90                  95

His Leu Val Ser Glu Val Arg Gly Met Gln Glu Ala Pro Glu Ala Ile
            100                 105                 110

Leu Ser Lys Ala Ile Glu Ile Glu Glu Gln Asn Arg Arg Leu Leu Glu
        115                 120                 125

Gly Met Glu Lys Ile Val Gly Gln Val Gln Pro Arg Ile Lys Glu Asn
    130                 135                 140

Glu Val Tyr Ser Val Trp Ser Gly Leu Pro Ser Leu Gln Met Ala Asp
145                 150                 155                 160

Glu Asp Ser Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Val Tyr Asp Ser Asn Cys
        195

(2) INFORMATION FOR SEQ ID NO:9:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Ile Pro Val Cys Pro Arg Gly Ser Val Arg Cys Gln Val Ser Leu Pro
1               5                  10                  15

Asp Leu Phe Asp Arg Ala Val Met Leu Ser His Tyr Ile His Ser Leu
            20                  25                  30

Ser Ser Asp Met Phe His Glu Phe Asn Lys Gln Tyr Ala Leu Gly Arg
        35                  40                  45
```

```
Gly Phe Ile Pro Arg Ala Ile Asn Ser Cys His Thr Ser Ser Ile Ser
 50                  55                  60

Thr Pro Glu Asp Lys Asp Gln Ala Gln Gln Thr His His Glu Val Leu
 65                  70                  75                  80

Met Asp Leu Ile Leu Gly Leu Leu Arg Ser Trp Asn Asp Pro Leu Asp
                 85                  90                  95

His Leu Ala Ser Glu Val His Ser Leu Pro Lys Ala Pro Ser Ala Leu
                100                 105                 110

Leu Thr Lys Ala Thr Glu Val Lys Glu Glu Asn Gln Arg Leu Leu Glu
            115                 120                 125

Gly Ile Glu Lys Ile Val Asp Gln Val His Pro Gly Ala Lys Glu Asn
130                 135                 140

Lys Ala Tyr Ser Val Trp Ser Gly Leu Pro Ser Leu Gln Thr Thr Asp
145                 150                 155                 160

Glu Asp Ala Arg Leu Phe Ala Phe Tyr Asn Leu Phe Arg Cys Leu Arg
                165                 170                 175

Arg Asp Ser His Lys Ile Asp Ser Tyr Leu Lys Leu Leu Lys Cys Arg
                180                 185                 190

Ile Val Tyr Asn Asn Asn Cys
195

(2) INFORMATION FOR SEQ ID NO:10:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Leu Pro Ile Cys Pro Ser Gly Ala Val Asn Cys Gln Val Ser Leu Arg
  1               5                  10                  15

Asp Leu Phe Asp Arg Ala Val Ile Leu Ser His Tyr Ile His Asn Leu
                 20                  25                  30

Ser Ser Glu Met Phe Asn Glu Phe Asp Lys Arg Tyr Ala Gln Gly Arg
             35                  40                  45

Gly Phe Met Thr Lys Ala Ile Asn Ser Cys His Thr Ser Ser Leu Ser
 50                  55                  60

Thr Pro Glu Asp Lys Glu Gln Ala Gln Gln Ile His His Glu Asp Leu
 65                  70                  75                  80

Leu Asn Leu Val Leu Arg Val Leu Arg Ser Trp Asn Asp Pro Leu Tyr
                 85                  90                  95

His Leu Val Thr Glu Val Arg Gly Met Gln Glu Ala Pro Asp Ala Ile
                100                 105                 110

Leu Ser Arg Ala Ile Glu Ile Glu Glu Gln Asn Lys Arg Leu Leu Glu
            115                 120                 125

Gly Met Glu Lys Ile Val Gly Gln Val His Pro Gly Val Lys Glu Asn
130                 135                 140

Glu Ile Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
                180                 185                 190
```

Ile Ile Tyr Asp Ser Asn Cys
        195

(2) INFORMATION FOR SEQ ID NO:11:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Thr Pro Val Cys Pro Asn Gly Pro Gly Asn Cys Gln Val Ser Leu Arg
1               5                   10                  15

Asp Leu Phe Asp Arg Ala Val Met Val Ser His Tyr Ile His Asn Leu
            20                  25                  30

Ser Ser Glu Met Phe Asn Glu Phe Asp Lys Arg Tyr Ala Gln Gly Lys
        35                  40                  45

Gly Phe Ile Thr Met Ala Leu Asn Ser Cys His Thr Ser Ser Leu Pro
50                  55                  60

Thr Pro Glu Asp Lys Glu Gln Ala Gln Gln Thr His His Glu Val Leu
65                  70                  75                  80

Met Ser Leu Ile Leu Gly Leu Leu Arg Ser Trp Asn Asp Pro Leu Tyr
                85                  90                  95

His Leu Val Thr Glu Val Arg Gly Met Lys Gly Val Pro Asp Ala Ile
            100                 105                 110

Leu Ser Arg Ala Ile Glu Ile Glu Glu Glu Asn Lys Arg Leu Leu Glu
        115                 120                 125

Gly Met Glu Met Ile Phe Gly Gln Val Ile Pro Gly Ala Lys Glu Thr
130                 135                 140

Glu Pro Tyr Pro Val Trp Ser Gly Leu Pro Ser Leu Gln Thr Lys Asp
145                 150                 155                 160

Glu Asp Ala Arg His Ser Ala Phe Tyr Asn Leu Leu His Cys Leu Arg
                165                 170                 175

Arg Asp Ser Ser Lys Ile Asp Thr Tyr Leu Lys Leu Leu Asn Cys Arg
            180                 185                 190

Ile Ile Tyr Asn Asn Asn Cys
        195

(2) INFORMATION FOR SEQ ID NO:12:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Leu Pro Ile Cys Pro Ser Gly Ala Val Asn Cys Gln Met Ser Leu Arg
1               5                   10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Ile Thr Lys Ala Ile Asn Ser Cys His Thr Ser Ser Leu Ser
50                  55                  60

```
Thr Pro Glu Asp Lys Glu Gln Ala Gln Gln Ile His His Glu Val Leu
65                  70                  75                  80

Leu Asn Leu Ile Leu Arg Val Leu Arg Ser Trp Asn Asp Pro Leu Tyr
                85                  90                  95

His Leu Val Thr Glu Val Arg Gly Met Gln Glu Ala Pro Asp Ala Ile
                100                 105                 110

Leu Ser Arg Ala Ile Glu Ile Glu Glu Gln Asn Lys Arg Leu Leu Glu
                115                 120                 125

Gly Met Glu Lys Ile Val Gly Gln Val His Pro Gly Ile Lys Glu Asn
    130                 135                 140

Glu Val Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Ile Tyr Asp Ser Asn Cys
                195
```

(2) INFORMATION FOR SEQ ID NO:13:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Thr Pro Val Cys Pro Asn Gly Pro Gly Asn Cys Gln Val Ser Leu Arg
1               5                   10                  15

Asp Leu Phe Asp Arg Ala Val Met Val Ser His Tyr Ile His Asp Leu
                20                  25                  30

Ser Ser Glu Met Phe Asn Glu Phe Asp Lys Arg Tyr Ala Gln Gly Lys
                35                  40                  45

Gly Phe Ile Thr Met Ala Leu Asn Ser Cys His Thr Ser Ser Leu Pro
    50                  55                  60

Thr Pro Glu Asp Lys Glu Gln Ala Gln Gln Thr His His Glu Val Leu
65                  70                  75                  80

Met Ser Leu Ile Leu Gly Leu Leu Arg Ser Trp Asn Asp Pro Leu Tyr
                85                  90                  95

His Leu Val Thr Glu Val Arg Gly Met Lys Gly Ala Pro Asp Ala Ile
                100                 105                 110

Leu Ser Arg Ala Ile Glu Ile Glu Glu Glu Asn Lys Arg Leu Leu Glu
                115                 120                 125

Gly Met Glu Met Ile Phe Gly Gln Val Ile Pro Gly Ala Lys Glu Thr
    130                 135                 140

Glu Pro Tyr Pro Val Trp Ser Gly Leu Pro Ser Leu Gln Thr Lys Asp
145                 150                 155                 160

Glu Asp Ala Arg Tyr Ser Ala Phe Tyr Asn Leu Leu His Cys Leu Arg
                165                 170                 175

Arg Asp Ser Ser Lys Ile Asp Thr Tyr Leu Lys Leu Leu Asn Cys Arg
                180                 185                 190

Ile Ile Tyr Asn Asn Asn Cys
                195
```

(2) INFORMATION FOR SEQ ID NO:14:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

```
Leu Pro Ile Cys Pro Ser Gly Ala Val Asn Cys Gln Val Ser Leu Arg
1               5                   10                  15

Asp Leu Phe Asp Arg Ala Val Ile Leu Ser His Tyr Ile His Asn Leu
            20                  25                  30

Ser Ser Glu Met Phe Asn Glu Phe Asp Lys Arg Tyr Ala Gln Gly Arg
        35                  40                  45

Gly Phe Ile Thr Lys Ala Ile Val Ser Cys His Thr Ser Ser Leu Ser
    50                  55                  60

Thr Pro Glu Asp Lys Glu Gln Ala Gln Gln Ser His His Glu Val Leu
65                  70                  75                  80

Val Ser Leu Ile Leu Gly Val Leu Arg Ser Trp Asn Asp Pro Leu Tyr
                85                  90                  95

His Leu Val Thr Glu Val Arg Gly Met Gln Glu Ala Pro Asp Ala Ile
            100                 105                 110

Leu Ser Arg Ala Ile Glu Ile Glu Glu Gln Asn Lys Arg Leu Leu Glu
        115                 120                 125

Gly Met Glu Lys Ile Val Gly Gln Val His Pro Gly Val Lys Glu Asn
    130                 135                 140

Glu Val Tyr Ser Val Trp Ser Gly Leu Pro Ser Leu Gln Met Ala Asp
145                 150                 155                 160

Glu Asp Thr Arg Leu Phe Ala Phe Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile Tyr Asp Ser Asn Cys
        195
```

(2) INFORMATION FOR SEQ ID NO:15:

(i) SEQUENCE CHARACTERISTICS:
        (A) LENGTH: 197 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Leu Pro Val Cys Ser Gly Gly Asp Cys Gln Thr Pro Leu Pro Glu Leu
1               5                   10                  15

Phe Asp Arg Val Val Met Leu Ser His Tyr Ile His Thr Leu Tyr Thr
            20                  25                  30

Asp Met Phe Ile Glu Phe Asp Lys Gln Tyr Val Gln Asp Arg Glu Phe
        35                  40                  45

Ile Ala Lys Ala Ile Asn Asp Cys Pro Thr Ser Ser Leu Ala Thr Pro
    50                  55                  60

Glu Asp Lys Glu Gln Ala Gln Lys Val Pro Pro Glu Val Leu Leu Asn
```

```
65                  70                  75                  80
Leu Ile Leu Ser Leu Val His Ser Trp Asn Asp Pro Leu Phe Gln Leu
                85                  90                  95
Ile Thr Gly Leu Gly Gly Ile His Glu Ala Pro Asp Ala Ile Ile Ser
                100                 105                 110
Arg Ala Lys Glu Ile Glu Glu Gln Asn Lys Arg Leu Leu Glu Gly Ile
                115                 120                 125
Glu Lys Ile Ile Ser Gln Ala Tyr Pro Glu Ala Lys Gly Asn Glu Ile
    130                 135                 140
Tyr Leu Val Trp Ser Gln Leu Pro Ser Leu Gln Gly Val Asp Glu Glu
145                 150                 155                 160
Ser Lys Asp Leu Ala Phe Tyr Asn Asn Ile Arg Cys Leu Arg Arg Asp
                165                 170                 175
Ser His Lys Val Asp Asn Tyr Leu Lys Phe Leu Arg Cys Gln Ile Val
                180                 185                 190
His Lys Asn Asn Cys
    195

(2) INFORMATION FOR SEQ ID NO:16:

(i) SEQUENCE CHARACTERISTICS:
        (A) LENGTH: 197 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Leu Pro Ile Cys Ser Ala Gly Asp Cys Gln Thr Ser Leu Arg Glu Leu
1               5                   10                  15
Phe Asp Arg Val Val Ile Leu Ser His Tyr Ile His Thr Leu Tyr Thr
                20                  25                  30
Asp Met Phe Ile Glu Phe Asp Lys Gln Tyr Val Gln Asp Arg Glu Phe
            35                  40                  45
Met Val Lys Val Ile Asn Asp Cys Pro Thr Ser Ser Leu Ala Thr Pro
    50                  55                  60
Glu Asp Lys Glu Gln Ala Leu Lys Val Pro Pro Glu Val Leu Leu Asn
65                  70                  75                  80
Leu Ile Leu Ser Leu Val Gln Ser Ser Ser Asp Pro Leu Phe Gln Leu
                85                  90                  95
Ile Thr Gly Val Gly Gly Ile Gln Glu Ala Pro Glu Tyr Ile Leu Ser
                100                 105                 110
Arg Ala Lys Glu Ile Glu Glu Gln Asn Lys Gln Leu Leu Glu Gly Val
                115                 120                 125
Glu Lys Ile Ile Ser Gln Ala Tyr Pro Glu Ala Lys Gly Asn Gly Ile
    130                 135                 140
Tyr Phe Val Trp Ser Gln Leu Pro Ser Leu Gln Gly Val Asp Glu Glu
145                 150                 155                 160
Ser Lys Ile Leu Ser Leu Arg Asn Thr Ile Arg Cys Leu Arg Arg Asp
                165                 170                 175
Ser His Lys Val Asp Asn Phe Leu Lys Val Leu Arg Cys Gln Ile Ala
                180                 185                 190
His Gln Asn Asn Cys
    195
```

(2) INFORMATION FOR SEQ ID NO:17:

(i) SEQUENCE CHARACTERISTICS:
        (A) LENGTH: 197 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Gln Pro Ile Cys Gln Asn Gly Gly Thr Asn Cys Gln Ile Pro Thr Ser
  1               5                  10                  15

Ala Leu Phe Asp Arg Ala Val Lys Leu Ser His Tyr Ile His Ser Leu
             20                  25                  30

Ser Ser Glu Met Phe Asn Glu Phe Asp Glu Arg Phe Thr Pro Gly Arg
         35                  40                  45

Arg Phe Leu Ala Lys Ser Gly Ile Ser Cys His Thr Ser Ser Leu Asn
     50                  55                  60

Thr Pro Glu Asp Lys Glu Ala Arg Gln Ile Gln His Glu Asp Leu Leu
 65                  70                  75                  80

Asn Leu Val Leu Lys Val Leu Arg Ser Trp Asn Asp Pro Leu Val His
                 85                  90                  95

Met Val Ser Glu Val Gln Asp Ile Arg Glu Ala Pro Asp Thr Ile Leu
             100                 105                 110

Trp Lys Thr Val Glu Val Glu Glu Gln Thr Lys Arg Leu Leu Glu Gly
         115                 120                 125

Met Glu Arg Ile Ile Gly Arg Ile Gln Pro Gly Asp Leu Glu Asn Glu
     130                 135                 140

Ile Tyr Ser Pro Trp Pro Gly Pro Ala Ser Ile Pro Gly Asp Glu Asn
145                 150                 155                 160

Ser Arg Leu Phe Ala Phe Tyr Asn Leu Leu His Cys Leu Arg Arg Asp
                165                 170                 175

Ser His Lys Ile Asp Asn Tyr Leu Lys Leu Lys Cys Arg Leu Ile
             180                 185                 190

His Glu Gly Asn Cys
             195
```

(2) INFORMATION FOR SEQ ID NO:18:

(i) SEQUENCE CHARACTERISTICS:
        (A) LENGTH: 187 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Val Gly Leu Asn Asp Leu Leu Glu Arg Ala Ser Gln Leu Ser Asp Lys
  1               5                  10                  15

Leu His Ser Leu Ser Thr Ser Leu Thr Asn Asp Leu Asp Ser His Phe
             20                  25                  30

Pro Pro Val Gly Arg Val Met Met Pro Arg Pro Ser Met Cys His Thr
         35                  40                  45

Ser Ser Leu Gln Ile Pro Asn Asp Lys Asp Gln Ala Leu Lys Ile Pro
     50                  55                  60

Glu Asp Glu Leu Leu Ser Leu Ala Arg Ser Leu Leu Leu Ala Trp Ser
 65                  70                  75                  80
```

```
Asp Pro Leu Ala Leu Leu Ser Ser Glu Ala Ser Ser Leu Ala His Pro
                85                  90                  95

Glu Arg Asn Thr Ile Asp Ser Lys Thr Lys Glu Leu Gln Asp Asn Ile
            100                 105                 110

Asn Ser Leu Gly Ala Gly Leu Glu His Val Phe Gln Lys Met Gly Ser
            115                 120                 125

Ser Ser Asp Glu Leu Ser Ser Leu Pro Phe Tyr Thr Ser Ser Leu Gly
            130                 135                 140

Gln Asp Lys Thr Ser Arg Leu Val Asn Phe His Asn Leu Leu Ser Cys
145                 150                 155                 160

Phe Arg Arg Asp Ser His Lys Ile Asp Ser Phe Leu Lys Val Leu Arg
                165                 170                 175

Cys Arg Ala Ala Lys Lys Arg Pro Glu Met Cys
                180                 185
```

(2) INFORMATION FOR SEQ ID NO:19:

(i) SEQUENCE CHARACTERISTICS:
        (A) LENGTH: 187 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Ile Gly Leu Ser Asp Leu Met Glu Arg Ala Ser Gln Arg Ser Asp Lys
1               5                   10                  15

Leu His Ser Leu Ser Thr Ser Leu Thr Lys Asp Leu Asp Ser His Phe
            20                  25                  30

Pro Pro Met Gly Arg Val Met Met Pro Arg Pro Ser Met Cys His Thr
            35                  40                  45

Ser Ser Leu Gln Thr Pro Lys Asp Lys Glu Gln Ala Leu Lys Val Ser
            50                  55                  60

Glu Asn Glu Leu Ile Ser Leu Ala Arg Tyr Leu Leu Leu Ala Trp Asn
65                  70                  75                  80

Asp Pro Leu Leu Leu Leu Ser Ser Glu Ala Pro Thr Leu Pro His Pro
                85                  90                  95

Ser Asn Gly Asp Ile Ser Ser Lys Ile Arg Glu Leu Gln Asp Tyr Ser
            100                 105                 110

Lys Ser Leu Gly Asp Gly Leu Asp Ile Met Val Asn Lys Met Gly Pro
            115                 120                 125

Ser Ser Gln Tyr Ile Ser Ser Ile Pro Phe Lys Gly Gly Asp Leu Gly
            130                 135                 140

Asn Asp Lys Thr Ser Arg Leu Ile Asn Phe His Phe Leu Met Ser Cys
145                 150                 155                 160

Phe Arg Arg Asp Ser His Lys Ile Asp Ser Phe Leu Lys Val Leu Arg
                165                 170                 175

Cys Arg Ala Thr Asn Met Arg Pro Glu Thr Cys
                180                 185
```

(2) INFORMATION FOR SEQ ID NO:20:

(i) SEQUENCE CHARACTERISTICS:
        (A) LENGTH: 188 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
Val Pro Ile Asn Glu Leu Phe Glu Arg Ala Ser Gln His Ser Asp Lys
 1               5                  10                  15

Leu His Ser Leu Ser Thr Thr Leu Thr Gln Glu Leu Asp Ser His Phe
                20                  25                  30

Pro Pro Ile Gly Arg Val Ile Met Pro Arg Pro Ala Met Cys His Thr
                35                  40                  45

Ser Ser Leu Gln Thr Pro Ile Asp Lys Asp Gln Ala Leu Gln Val Ser
50                  55                  60

Glu Ser Asp Leu Met Ser Leu Ala Arg Ser Leu Leu Gln Ala Trp Ser
65                  70                  75                  80

Asp Pro Leu Val Val Leu Ser Ser Ala Ser Thr Leu Pro His Pro
                85                  90                  95

Ala Gln Ser Thr Ile Phe Asn Lys Ile Gln Glu Met Gln Gln Tyr Ser
                100                 105                 110

Lys Ser Leu Lys Asp Gly Leu Asp Val Leu Ser Ser Lys Met Gly Ser
                115                 120                 125

Pro Ala Gln Ala Ile Thr Ser Leu Pro Tyr Arg Gly Gly Thr Asn Leu
130                 135                 140

Gly His Asp Lys Ile Thr Lys Leu Ile Asn Phe Asn Phe Leu Leu Ser
145                 150                 155                 160

Cys Leu Arg Arg Asp Ser His Lys Ile Asp Ser Phe Leu Lys Val Leu
                165                 170                 175

Arg Cys Arg Ala Ala Lys Met Gln Pro Glu Met Cys
                180                 185
```

(2) INFORMATION FOR SEQ ID NO:21:

(i) SEQUENCE CHARACTERISTICS:
        (A) LENGTH: 177 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:21:

```
Val Pro Ile Asn Asp Leu Ile Tyr Arg Ala Ser Gln Gln Ser Asp Lys
 1               5                  10                  15

Leu His Ala Leu Ser Ser Met Leu Thr Gln Glu Leu Gly Ser Glu Ala
                20                  25                  30

Phe Pro Ile Asp Arg Val Leu Ala Cys His Thr Ser Ser Leu Gln Thr
                35                  40                  45

Pro Thr Asp Lys Glu Gln Ala Leu Gln Val Ser Glu Ser Asp Leu Leu
50                  55                  60

Ser Leu Ala Arg Ser Leu Leu Gln Ala Trp Ser Asp Pro Leu Glu Val
65                  70                  75                  80

Leu Ser Ser Ser Thr Asn Val Leu Pro Tyr Ser Ala Gln Ser Thr Leu
                85                  90                  95

Ser Lys Thr Ile Gln Lys Met Gln Glu His Ser Lys Asp Leu Lys Asp
                100                 105                 110

Gly Leu Asp Ile Leu Ser Ser Lys Met Gly Pro Ala Ala Gln Thr Ile
                115                 120                 125

Thr Ser Leu Pro Phe Ile Glu Thr Asn Glu Ile Gly Gln Asp Lys Ile
130                 135                 140
```

```
Thr Lys Leu Leu Ser Cys Phe Arg Arg Asp Ser His Lys Ile Asp Ser
145                 150                 155                 160

Phe Leu Lys Val Leu Arg Cys Arg Ala Ala Asn Met Gln Pro Gln Val
                165                 170                 175

Cys
```

(2) INFORMATION FOR SEQ ID NO:22:

(i) SEQUENCE CHARACTERISTICS:
        (A) LENGTH: 191 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

```
Thr Phe Pro Thr Met Pro Leu Ser Asn Leu Phe Thr Asn Ala Val Leu
1               5                   10                  15

Arg Ala Gln His Leu His Leu Leu Ala Ala Glu Thr Tyr Lys Glu Phe
                20                  25                  30

Glu Arg Thr Tyr Ile Pro Glu Asp Gln Arg Tyr Thr Asn Lys Asn Ser
            35                  40                  45

Gln Ala Ala Phe Cys Tyr Ser Glu Thr Ile Pro Ala Pro Thr Gly Lys
50                  55                  60

Asp Asp Ala Gln Gln Lys Ser Asp Met Glu Leu Leu Arg Phe Ser Leu
65                  70                  75                  80

Val Leu Ile Gln Ser Trp Leu Thr Pro Val Gln Tyr Leu Ser Lys Val
                85                  90                  95

Phe Thr Asn Asn Leu Val Phe Gly Thr Ser Asp Arg Val Phe Glu Lys
                100                 105                 110

Leu Lys Asp Leu Glu Glu Gly Ile Gln Ala Leu Met Arg Glu Leu Glu
            115                 120                 125

Asp Arg Ser Pro Arg Gly Pro Gln Leu Leu Arg Pro Thr Tyr Asp Arg
130                 135                 140

Phe Asp Ile His Leu Arg Ser Glu Asp Ala Leu Leu Lys Asn Tyr Gly
145                 150                 155                 160

Leu Leu Ser Cys Phe Lys Lys Asp Leu His Lys Val Glu Thr Tyr Leu
                165                 170                 175

Lys Val Met Lys Cys Arg Arg Phe Gly Glu Ser Asn Cys Asn Ile
                180                 185                 190
```

(2) INFORMATION FOR SEQ ID NO:23:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:23:

```
Pro Ser Cys Gly Pro Asp Val Phe Val Ser Leu Arg Lys Ser Phe Thr
1               5                   10                  15

Asp Arg Phe Met Asn Ala Ala Ser Leu Ser His Asp Phe Tyr Asn Leu
                20                  25                  30

Ser Thr Ile Met Phe Asn Glu Phe Asp Glu Lys Tyr Ala Gln Gly Lys
            35                  40                  45
```

-continued

```
Leu Tyr Tyr Ile Asn Val Thr Lys Ser Cys His Thr Asn Ser Phe His
    50                  55                  60

Ala Pro Glu Glu Arg Asp Ile Val Gln Gln Thr Asn Ile Glu Asp Leu
65                  70                  75                  80

Ser Lys Trp Thr Leu Val Leu Val Tyr Ser Trp Asn Asn Pro Leu His
                85                  90                  95

His Leu Val Thr Glu Leu Gln His Met Lys Glu Leu Ser Asn Ala Phe
                100                 105                 110

Leu Ser Ser Ala Thr Arg Phe Glu Asn Met Ser Glu Lys Leu Gln Ala
            115                 120                 125

Phe Ile Glu Arg Gln Phe Ser Lys Ile Ile Val Pro Val Leu Asn Thr
        130                 135                 140

Met Ile Gln Ala Arg Ser Ser Trp Thr Gly Leu Pro Ser Leu Met Ser
145                 150                 155                 160

Ser Ala Glu Asp Arg Arg His Ser Glu Phe Tyr Asn Leu Phe Tyr Cys
                165                 170                 175

Leu Arg Arg Asp Ser Arg Lys Val Asp Met Tyr Ile Lys Ile Leu Thr
                180                 185                 190

Cys Arg Thr His Lys Thr Cys
            195
```